United States Patent [19]

Romano

[11] Patent Number: 5,207,214
[45] Date of Patent: May 4, 1993

[54] SYNTHESIZING ARRAY FOR THREE-DIMENSIONAL SOUND FIELD SPECIFICATION

[76] Inventor: Anthony J. Romano, 521 E St., NE., Washington, D.C. 20002

[21] Appl. No.: 671,464

[22] Filed: Mar. 19, 1991

[51] Int. Cl.$^5$ .............................................. A61B 17/22
[52] U.S. Cl. ........................... 128/24 AA; 128/24 EL; 367/138; 367/155
[58] Field of Search ....................... 128/660.01, 660.03, 128/24 AA, 24 EL, 804; 606/128; 367/138, 155, 157

[56] References Cited

U.S. PATENT DOCUMENTS

| | | | |
|---|---|---|---|
| 4,526,168 | 7/1985 | Hassler et al. | |
| 4,589,415 | 5/1986 | Haaga | 128/328 |
| 4,803,995 | 2/1989 | Ishida et al. | 128/660.01 |
| 4,823,773 | 4/1989 | Naser et al. | 128/24 A |
| 4,844,081 | 7/1989 | Northeved et al. | 128/660.03 |
| 4,858,597 | 8/1989 | Kurtze et al. | 128/24 A |
| 4,907,573 | 3/1990 | Nagasaki | 128/24 A |
| 4,913,156 | 4/1990 | Inbar et al. | 128/660.03 |
| 4,962,754 | 10/1990 | Okazaki | 128/24 A |
| 4,986,259 | 1/1991 | Aida et al. | 128/24 A |
| 5,092,336 | 3/1992 | Fink | 128/660.07 |

OTHER PUBLICATIONS

R. E. Apfel, "Possibility of Microcavitation from Diagnostic Ultrasound," IEEE Transactions on Ultrasonics, Ferroelectrics, and Frequency Control, vol. UFFC-33, No. 2, Mar. 1986.

A. J. Carmichael, M. M. Mossoba, P. Riesz, C. L. Christman, "Free Radical Production in Aqueous Solutions Exposed to Simulated Ultrasonic Diagnostic Conditions," IEEE Transactions on Ultrasonics, Ferroelectrics, and Frequency Control, vol. UFFC-33, No. 2, Mar. 1986.

H. G. Flynn, "A Mechanism for the Generation of Cavitation Maxima by Pulsed Ultrasound," J. Acoust. Soc. Am 76(2), Aug. 1984.

H. G. Flynn, "Generation of Transient Cavities in Liquids by Microsecond Pulses of Ultrasound," J. Acoust. Soc. Am 72(6), Dec. 1982.

K. Makino, M. M. Mossoba and P. Riesz, "Chemical Effects of Ultrasound on Aqueous Solutions. Formation of Hydroxyl Radicals and Hydrogen Atoms," J. Phys. Chem. 87, 1983.

B. Widrow, R. G. Winter, R. A. Baxter, "Layered Neural Nets for Pattern Recognition," IEEE Transactions on Acoustics, Speech, and Signal Processing, vol. 36, No. 7, Jul. 1988.

A. S. Gevins, N. H. Morgan, "Applications of Neural--Network (NN) Signal Processing in Brain Research," IEEE Transactions on Acoustics, Speech, and Signal Processing, vol. 36, No. 7, Jul. 1988.

R. P. Gorman, T. J. Sejnowski, "Learned Classification of Sonar Targets Using a Massively Parallel Network," IEEE Transactions on Acoustics, Speech and Signal Processing, vol. 36, No. 7, Jul. 1988.

P. He, "Acoustic Attenuation Estimation for Soft Tis- (List continued on next page.)

*Primary Examiner*—Ruth S. Smith
*Attorney, Agent, or Firm*—Baker & Botts

[57] ABSTRACT

A non-invasive, synthesizing array of "N" reciprocal transducers is driven by "N" linearly independent inputs for three-dimensional sound field specification at "N" locations either within, or on, an isotropic or anisotropic acoustic/elastodynamic medium. Towards these ends, the impulse response, or Dyadic Green's Function Matrix, characteristic of the medium is determined, and the desired sound field response at "N" locations either within, or on, the surface of the medium is specified. This results in a system of "N" equations, which can be solved to obtain the "N" linearly independent inputs required to create the "N" desired, three-dimensional sound field responses. This permits precise focusing and spatial manipulation of sound intensity, as well as amplitude control within a specific volume or region of convergence within, or on, the medium.

50 Claims, 3 Drawing Sheets

OTHER PUBLICATIONS sue from Ultrasound Echo Envelope Peaks," IEEE Transactions on Ultrasonics, Ferroelectrics, and Frequency Control, vol. 36, No. 2, Mar. 1989.

Y. Yamakoski, J. Sato, T. Sato, "Ultrasonic Imaging of Internal Vibration of Soft Tissue under Forced Vibration," IEEE Transactions on Ultrasonics, Ferroelectrics, and Frequency Control, vol. 37, No. 2, Mar. 1990.

L. J. Slutsky, "On the Possible Contribution of Chemical Relaxation to Acoustic Absorption in Biological Systems," IEEE Translations on Ultrasonics, Ferroelectrics, and Frequency Control, vol. UFFC-33, No. 2, Mar. 1986.

M. E. Barnard, M. J. Lancaster, E. G. S. Paige, "The Focusing of Surface-Acoustic-Waves Launched from a Slanted Chirped Transducer: I—Isotropic Substrate," IEEE Transactions on Ultrasonics, Ferroelectrics, and Frequency Control, vol. UFFC-36, No. 2, Sep. 1989.

M. J. Lancaster, E. G. S. Paige, "The Focusing of Surface Acoustic Waves Launched from a Slanted Chirped Transducer: II. Anisotropic Substrate," IEEE Transactions on Ultrasonics, Ferroelectrics, and Frequency Control, vol. 37, No. 2, May 1990.

M. Nikoonahad, M. V. Iravani, "Focusing Ultrasound in Biological Media," IEEE Transactions on Ultrasonics, Ferroelectrics, and Frequency Control, vol. 36, No. 2, Mar. 1989.

P. J. Benkeser, T. L. Pao, Y. J. Yoon, "Ultrasonic Phase Array Controller for Hyperthermia Applications," Ultrasonics, vol. 29, Jan. 1991.

A. J. Romano, "Three-Dimensional Image Reconstruction in Audio," J. Audio Eng. Soc., 35, No. 10 (1987).

A. J. Romano, "Linear Systems Approach to Image Source Representations of the Sound Fields in Enclosures," Ph.D. Thesis, Penn State University (1986).

SYNTHESIZING ARRAY FOR THREE-DIMENSIONAL SOUND FIELD SPECIFICATION

BACKGROUND OF THE INVENTION

1. Field of The Invention

This invention relates to a method and an apparatus for precisely specifying a sound field at various locations within a medium (e.g., a human body or an acoustical cavity), through the independent manipulation of inputs to a synthesizing array of reciprocal transducers. The invention can be used, for example, to destroy calculi, while simultaneously specifying a safe level of sound intensity in the area immediately surrounding the calculi, as well as in the intermediary tissue between the transducers and the calculi. In addition, objects and fluids can be acoustically levitated in microgravity or other environments through the utilization of this same principle.

2. Description of the Prior Art

In the prior art, it is known to use a large number of piezoelectric elements arranged in a mosaic pattern on a spherical surface so that ultrasonic waves transmitted from the elements converge on a single point. This is shown, for example, in U.S. Pat. No. 4,907,573 issued to Nagasaki. With reference to FIG. 1 of the present invention, there is shown such an arrangement of transducers. The piezoelectric elements 1 collectively constitute a transducer 2 which is applied to a subject 5 through a liquid bag 4 filled with an ultrasonic transmission medium 3, such as water, so that ultrasonic shock waves generated by the piezoelectric elements converge, for example, on a diseased portion existing in a kidney 6 or a calculus 7 to be treated and to thereby break it up. The water is used as an acoustic transmission medium in order that the ultrasonic shock waves do not attenuate during its propagation.

The ultrasonic shock wave is generated by applying a driving impulse voltage to the piezoelectric elements from a driving pulse generator 8. A mechanical-scanning type ultrasonic probe 9 and an ultrasonic diagnosis device 10 coupled to the probe may be provided for the purposes of locating the calculus.

Conventional non-invasive medical lithotripsy methods generally utilize either a focused array of transducers, each emanating sound amplitude levels (required for calculi destruction) that are extremely large, and/or a method for focusing an array of transducers, each emanating a relatively smaller sound amplitude level, such that large sound amplitude levels occur only in a region near the calculi to be destroyed.

For example, U.S. Pat. No. 4,526,168 issued to Hassler et al. discloses an apparatus for destroying calculi in body cavities. Hassler uses an ultrasonic transmitter 13 coupled with a number of time delay devices (7-11) to adjust the distance of focus so as to dispose the focus at the location of the calculus 6 of a kidney 5. Hassler, therefore, uses the same input to drive all of his transducers and focus all of his transducers at a single point.

U.S. Pat. No. 4,907,573 issued to Nagasaki discloses an ultrasonic lithotresis apparatus. This apparatus includes a driver circuit 8 for driving each of a plurality of transducers which are focused to converge at a single point. Delay lines 14 are adapted to finely shift the phases of the drive pulses from pulser 13 so that the phases of the transducers coincide with each other at the point of convergence.

Similar apparati are disclosed in U.S. Pat. No. 4,823,773 issued to Naser et al. and U.S. Pat. No. 4,858,597 issued to Kurtze et al.

A drawback of the prior art is that each transducer element within the array is driven by the same input signal, either in phase or time delayed with respect to the others. Additionally, the medium between each transducer and the intended focus is assumed to be homogeneous for each transducer. These factors are reasons why the resulting shock wave pulse is not very effective and why numerous repetitions of the pulse are needed for successful destruction of a calculus. Moreover, since the region of convergence of this resultant, large amplitude sound field cannot be precisely guaranteed, but only insinuated, i.e., since an isotropic, homogeneous medium is assumed to represent the actual anisotropic, inhomogeneous medium, and since each source is driven by the same input signal, these methods may result in the bruising and damaging of tissue and to cavitation, causing free-radical production, as well as pain to the victim, all of which are undesirable.

SUMMARY OF THE INVENTION

It is an object of the present invention to overcome these and other drawbacks of the prior art.

It is another object of this invention to provide a method and an apparatus, which permits the precise specification of the sound field at various locations within, or on, a medium, such that focusing of sound energy can be accurately realized, as well as providing for the ability to avoid extraneous or intermediary tissue damage due to cavitation effects in biomedical applications.

It is another object to provide a method and apparatus which supplies independent inputs to a plurality of transducers to achieve the above objects.

It is another object to provide adaptive control to enable the inputs of the transducers to be varied depending on changing conditions within the system.

It is a further object of the present invention to enable control of the vibrational modes (i.e., longitudinal modes, shear modes, torsional modes, spherical harmonics, etc.) of fluids and objects, permitting:

- the destruction of calculi, cancerous tissue, atherosclerotic plaque, vascular thrombi and/or emboli, etc., by forcing these materials and fluids into precise, uncharacteristic or extreme plastic deformation for their disintegration, or cause extreme, localized, internal frictional effects leading to heat production for vaporization;
- generalized non-invasive, percutaneous energy transfer;
- generalized movement of fluids (flow) and objects in microgravity or other environments; and
- the precise, non-invasive control of the position, movement, and rate of mixture of individual fluid droplets and/or chemicals in microgravity or other environments.

In order to carry out these and other novel aspects of the present invention there is provided a synthesizing array of reciprocal transducers, wherein each transducer element emanates a linearly independent, safe level of sound amplitude, based on a predicted and/or measured actual impulse response (Green's Function) characteristic of the isotropic or anisotropic medium to realize three-dimensional sound field construction.

In the case of biomedical applications, this permits the accurate focusing of intense sound energy without causing extraneous tissue damage. This allows precise sound intensity specification at various points, while simultaneously protecting other areas from large amplitude superposition which would result in bruising and cavitation.

In the case of generalized movement of fluids (flow) and objects in microgravity or other environments, this permits the specification of a generalized region or volume of convergence of a sound field. This will allow the non-invasive manipulation of the modes of vibration of fluid droplets, chemicals, and various objects, as well as their relative spatial positioning as functions of time.

In brief, a synthesizing array is a collection or distribution of sources of sound (transducers), whose individual input signals are linearly independent and can be individually controlled and varied simultaneously. With the proper inputs to a number, "N", of sources, the outputs from the distribution of sources can be superposed to create "N" points of desired sound responses. This principle can be used to focus sound intensely at specific locations and to simultaneously specify areas of zero or low sound amplitude at other locations. Alternatively, it may be used to specify regions of convergence leading to controlled vibrational behaviour of various objects and fluids.

According to one embodiment of the present invention, these and other objects may be carried out by determining from measurement and calculation the acoustical impulse response (or Green's Function) from each of "N" reciprocal transducers at a number of points within the medium, specifying the desired sound field at "N" location within this same medium, and solving a set of N×N equations to obtain the "N", linearly independent inputs needed for each of the "N" reciprocal transducers in the array, whose superposition will yield the desired sound field responses.

According to another novel aspect of the invention, the system may be made adaptive (e.g. through the use of adaptive algorithms and neural networks), such that the effects of fluctuations within the medium on the impulse response (or Green's Function), such as heart rate, respiration, etc., are continually and simultaneously updated (in real time) for even more accurate control of the desired sound field.

More specifically, a very large sound intensity level can be specified at a single point, while simultaneously specifying a zero or low sound intensity level in the surrounding or intermediary volume. Some of the possible uses of the invention include non-invasive medical diagnostics, tissue characterization, energy transfer, generalized destruction of calculi (i.e. lithotripsy), medical imaging, and acoustic levitation of objects and fluids in microgravity environments.

It is further proposed that with adequate spatial resolution and sufficient sound energy transfer to create controlled and localized intense heat production (localized hyperthermia), this technique could be extended to non-invasively identify and clear atherosclerotic plaque, vascular thrombi and emboli, as well as to induce cauterization and to destroy cancerous tissue and small tumors.

DESCRIPTION OF THE PREFERRED EMBODIMENT

Figure 2:
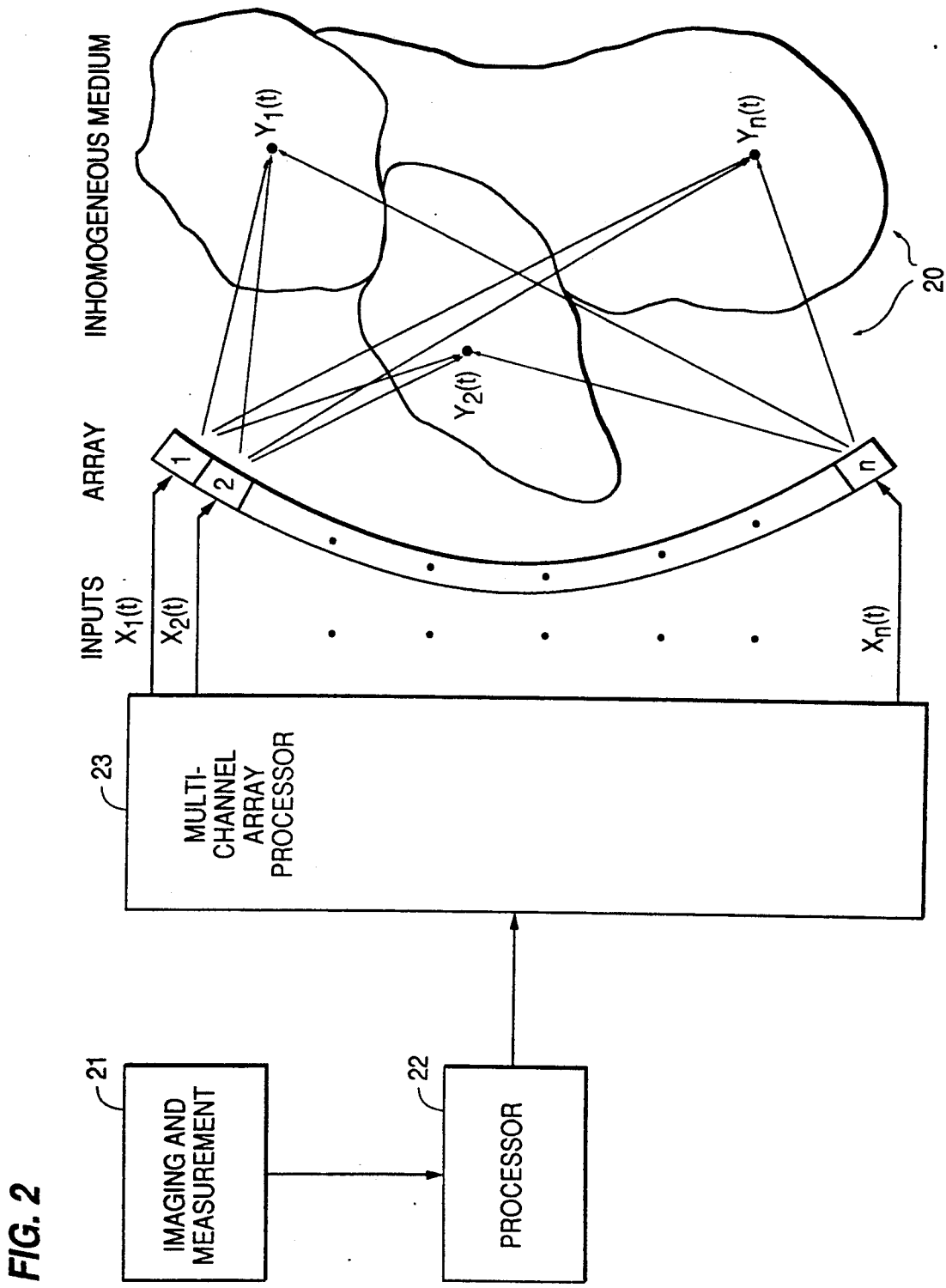
FIG. 2 is a diagrammatic illustration of an apparatus according to one embodiment of the present invention.

With reference to FIG. 2, for example, there is shown one embodiment of an apparatus for carrying out the present invention. In FIG. 2, there is shown a plurality of transducers 1-n operatively disposed with respect to an inhomogeneous medium, preferably a fluid medium, to enable sound waves to be transmitted from the transducers 1-n to a subject or object indicated generally as 20. The sound waves can be used, e.g., for destruction of a target located within the subject or object. In order to prevent unnecessary damage to the area around the target or to the area between transducers and the target, one aspect of the present invention is directed to determining a unique impulse response, or Green's Function, characteristic of the medium between each transducer and each field point $Y_1 - Y_n$.

This may be accomplished, for example, by using imaging and measurement means 21 and processor means 22 (described below). The processor means 22 supplies information to a multi-channel array processor 23 which in turn generates transducer inputs $X_1(t) - X_n(t)$.

The present invention may be used in a variety of applications, one of which is a biomedical application. In the case of a biomedical application, for example, the subject or object may be a patient, the target may be a calculi located within the patient's body and the medium may be characterized as an anisotropic, or rather an inhomogeneous medium. In order to determine the inputs for the synthesizing array, the Green's Function characteristic of the anisotropic medium must be determined to accurately define the acoustic response within this medium. In general, the determination of a unique solution for the inverse problem, or rather the determination of a unique Green's Function, is virtually impossible given only the limited information of the sound field on a surface enclosing a medium. More information could be obtained, i.e., the sound field "inside" the medium could be obtained invasively, however, it is preferable to obtain this information in a non-invasive manner.

Figure 3:
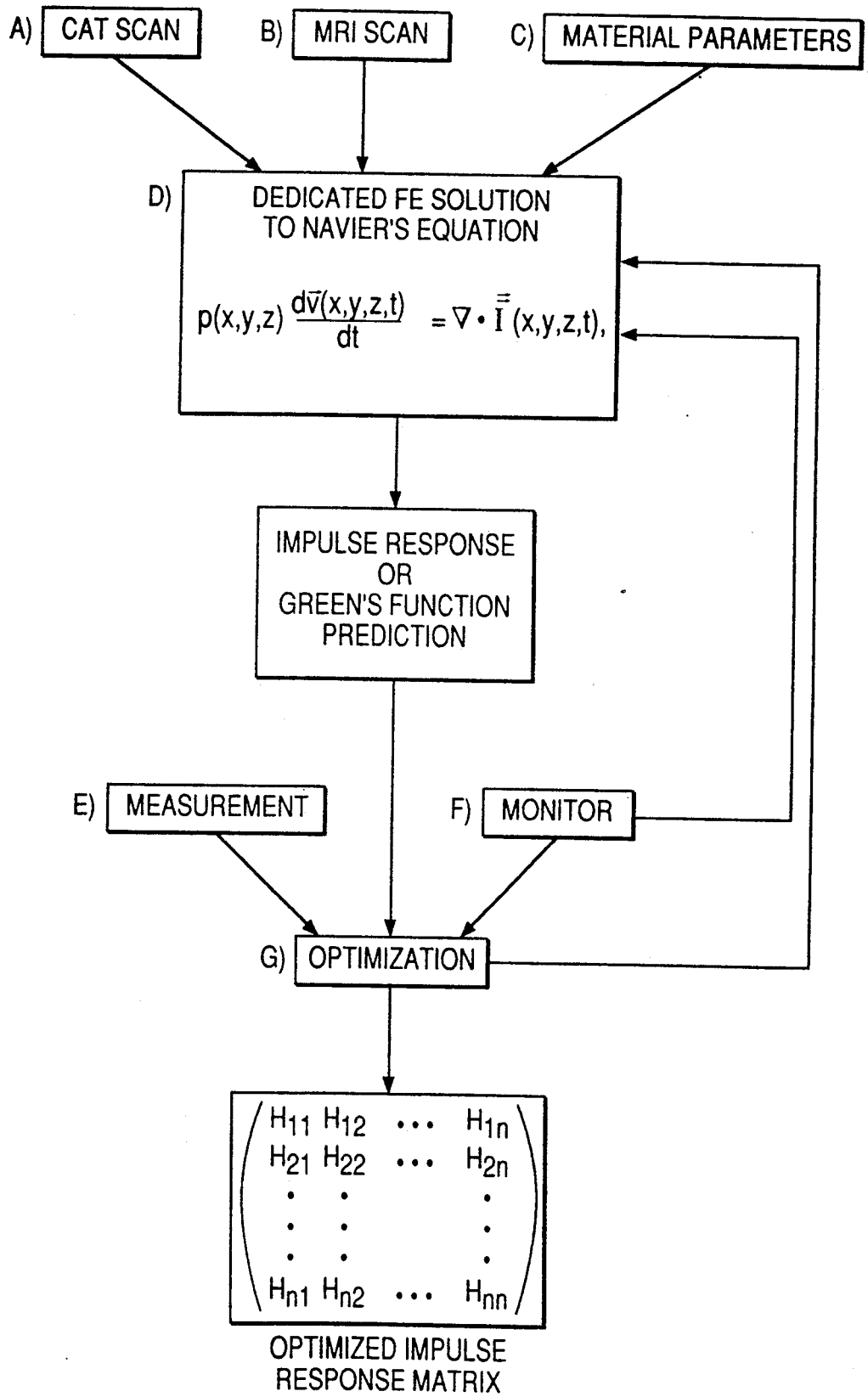
FIG. 3 diagrammatically illustrates one example of the steps which may be taken for the determination of the impulse response (or Green's Function) from each transducer element to each specified sound field location, according to an embodiment of the present invention.

As schematically depicted in FIG. 3, the imaging and measurement means 21 may be used to determine this information (in a known manner) by using one or more of the following techniques:

A. A CAT scan (Computed Axial Tomography), of the body or region under scrutiny, to obtain interior tissue and fluid spatial boundary definition, which is used to define the boundary conditions and spatial regions of material and fluid location necessary for the numerical solution described below, B. an MRI scan (Magnetic Resonance Imaging), of the body or region under scrutiny, to obtain, as in (A), interior tissue and fluid spatial boundary definition, which is used to further refine, resolve and define the boundary conditions and spatial regions of material and fluid location necessary for the numerical solution below, C. an empirical measurement of the acoustical parameters ($\rho$, E, $\nu$, $\eta$) (where $\rho$ = density, E = Young's modulus, $\nu$ = Poisson's ratio, and $\eta$ = damping (and/or viscosity, and/or the coefficient of expansive friction) of every tissue and fluid (or only selected ones) in a human body (using, for example, samples taken from cadavers or living subjects), such that the appropriate constants can be assigned to the appropriate spatial regions defined in (A) and (B) above, necessary for the numerical solution described below, D. a massively parallel processing computer system, e.g., 22, dedicated to the finite element solution to Navier's Equation:

$$\rho(x,y,z) \frac{d\vec{v}(x,y,z,t)}{dt} = \nabla \cdot \vec{I}(x,y,z,t), \quad \text{(Equation 1)}$$

where $\rho(x,y,z)$ is the local density of the medium, $\vec{v}(x,y,z,t)$ is the local particle velocity, and $\vec{I}(x,y,z,t)$ is the local stress tensor of the medium, for the prediction of the impulse response or Green's Function characteristic of the medium, E. measurements of the $N^2$ impulse responses between each of the reciprocal transducers on the surface enclosing the anisotropic medium, such that comparisons can be made between actual and predicted values for correction and optimization of the predicted impulse response or Green's Function, F. adaptive signal processing to monitor, e.g. respiration, heart rate, and blood pressure for continual updates of the $N^2$ impulse responses required, G. adaptive and optimal methods, i.e. neural networks to "learn" and optimize the system.

Based on a combination of these factors, a highly accurate prediction of the impulse response, or Green's Function anywhere within the body can be obtained. With reference to FIG. 3, this prediction is accomplished in the following manner.

Based on steps (A) and (B), high resolution, spatial maps of the boundaries of various tissues and fluids within the medium can be created in a known manner. This information, together with step (C), is input into processor means 22, step (D), which yields a numerical first approximation to the Green's Function. Steps (E) and (F) are used to yield corrected or actual comparative updates, and step (G) optimizes the system subject to these real updates.

Optimization of the system is accomplished by minimizing the errors between the predicted impulse responses and the actual, measured impulse responses. Assuming:

1. that Navier's equation of motion (Equation 1) is appropriate for the description of sound propagation in the anisotropic medium,
2. that the acoustical responses of the sources are accurately modelled,
3. that the CAT and MRI measurements are correct and accurate,
4. that the Finite Element (FE) implementation of all this is correct, and
5. the measurements are accurate, then the remaining variables causing any errors between the predicted and actual impulse responses will be due to differences between the previously measured material parameters, and the actual material parameters, and fluctuations in heart rate, blood pressure, and respiration, effecting the flow terms, $\vec{v} \cdot \nabla \vec{v}$, in Equation (1), resulting from the total derivative of the velocity, since $$\frac{d\vec{v}}{dt} = \frac{\partial \vec{v}}{\partial t} + \vec{v} \cdot \nabla \vec{v} \quad \text{Equation (2)}$$

In the case of the material parameters, optimization of their estimation can be realized, for example, by varying or perturbing the first estimate of the material constants according to the best-fit parameters yielded by well-known Maximum Likelihood Estimator algorithms, subject to the constraints of the extreme limits of actual material constant fluctuation, and the desired error minimization.

In the case of fluctuations in heart rate, blood pressure, and respiration, adaptation can be realized, for example, by using well known Adaptive Neural Networks using the LMS algorithm (Least Means Squares algorithm, or the Widrow-Hoff Delta Rule) which can easily be implemented to monitor or learn the time-dependent behavior of the system. See, e.g., article entitled "Layered Neural Nets for Pattern Recognition", written by Bernard Widrow, Rodney G. Winter, and Robert A. Baxter, published in *IEEE Transactions on Acoustics, Speech, And Signal Processing*, Vol. 36, No. 7, Jul. 1988. With this information, a running update of the impulse response predictions can be obtained, by continually comparing the flow terms, $\vec{v} \cdot \Delta \vec{v}$ in Equation (1), with actual, measured updates. This results in yet another constraint imposed upon our Green's Function optimization.

With the Green's Function having been obtained, there remain the tasks of specifying the desired sound fields, and determining the necessary inputs to the array of transducers to produce these desired sound fields.

Figure 1:
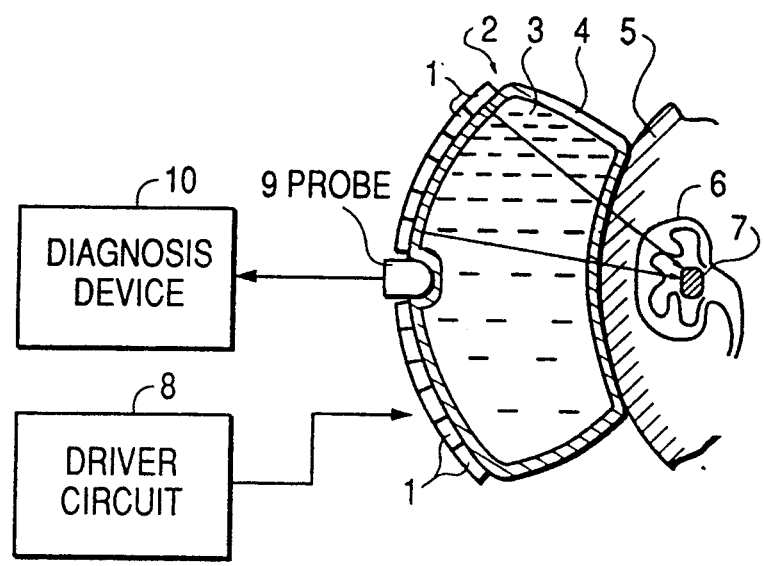
FIG. 1 is a diagrammatic illustration of a prior art ultrasonic lithotresis apparatus.
Figure 4:
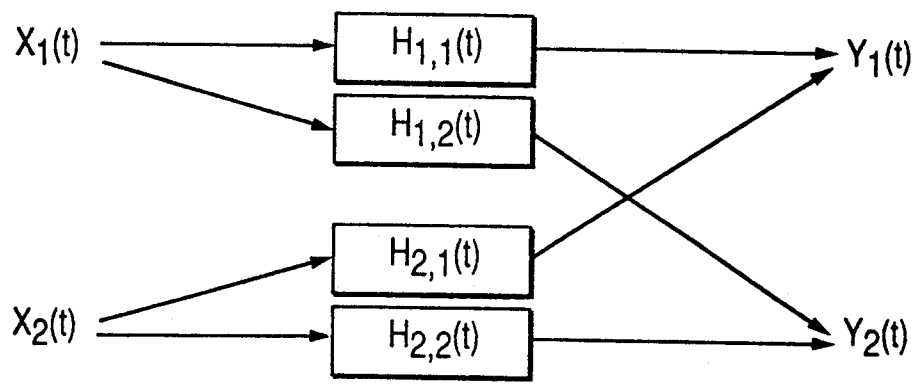
FIG. 4 illustrates a simplified example of an embodiment of the present invention with two inputs and two outputs.

To give a simplified example, reference is made to FIG. 4. For the purpose of this example only, it will be assumed that transducers 1 and 2 are the only two transducers used. Furthermore, it will be assumed that there are two points for which the desired sound field responses, $Y_1(t)$ and $Y_2(t)$, are specified. Of course, it is to be understood that more than two transducers and two points can be used in the preferred embodiment of the invention, and preferably N transducers are used and N field points are specified. In the example, we may express the two input/two output linear system mathematically as follows:

$$X_1(t) * H_{1,1}(t) + X_2(t) * H_{2,1}(t) = Y_1(t), \quad \text{Equation (3)}$$
$$X_1(t) * H_{1,2}(t) + X_2(t) * H_{2,2}(t) = Y_2(t) \quad \text{Equation (4)}$$

where $X_1(t)$ and $X_2(t)$ are the time dependent inputs to sources 1 and 2, respectively, where the symbol $H_{i,j}(t)$ corresponds to the time dependent impulse response, or Green's Function from source i to the specified field point j, and where the symbol * denotes convolution. Application of a Fourier transform to equations 3 and 4, and rearrangement yields $$\begin{pmatrix} X_1(f) \\ X_2(f) \end{pmatrix} = \begin{pmatrix} H_{1,1}(f) & H_{2,1}(f) \\ H_{1,2}(f) & H_{2,2}(f) \end{pmatrix}^{-1} \begin{pmatrix} Y_1(f) \\ Y_2(f) \end{pmatrix}. \quad \text{Equation (5)}$$

Once equation 5 has been solved for $X_1(f)$ and $X_2(f)$ for every frequency within the band dictated by the physical system and the desired sound fields, the necessary time dependent inputs, $X_1(t)$ and $X_2(t)$, can be obtained by performing an inverse Fourier transform on the sequences $X_1(f)$ and $X_2(f)$.

Therefore, by setting up the matrix as shown above, the inputs $X_1(t)$ and $X_2(t)$ can be determined for specified values of $Y_1(t)$ and $Y_2(t)$, which are the desired or specified outputs. Similarly, $H_{1,1}(t)$, $H_{1,2}(t)$, $H_{2,1}(t)$ and $H_{2,2}(t)$ correspond to the impulse response, or Green's Function Matrix components. These values are determined in the manner described above and in conjunction with FIG. 3. In this way, the actual inputs needed for the plurality of transducers can be determined according to a very precise specification so that the desired output at a plurality of points can be achieved.

Of course, as the number of transducers increases, the corresponding impulse response matrix and number of points whose output can be specified increases concomitantly. However, the same principle used above with respect to a two input, two output system can be applied to an N x N system.

Returning to the example, and FIG. 4, once $X_1(t)$ and $X_2(t)$ are determined, these functions can be provided as the independent inputs. Of course, if N inputs are specified, N independent inputs can be provided in a manner known in the art. Preferably, a massive, multiple input-/multiple output, dedicated array processor 23, with N independent channels is used to handle the inputs for, as well as the outputs from, each of the reciprocal transducers.

After the inputs have been provided to the array of transducers, a comparison of the actual resultant sound field, as received by each of the reciprocal transducers, can be compared to the predicted values, to determine fluctuations and updates or the Green's Function. These comparisons, as discussed previously in the section on optimization, may be sufficient to determine variations in the Green's Function caused by calculi destruction calculi displacement, etc. Ultimately, however, the entire imaging and measurement process may need to be repeated (or simply CAT and/or MRI procedures only) for verification of the success of the calculi destruction.

In operation, depending upon the biomedical application, the apparatus for implementing the above could be either:

a. a fluid filled, cylindrical (or other) cavity;
b. a pressurized vest; or
c. any focusing array of reciprocal transducers, yielding sufficient causal and linear impulse response features within the medium, for the realization of the desired outputs, with a distribution of numerous reciprocal transducers (a number "N", as required by the number of field points specified) either on the inner surface of the cavity or vest, or in or on any other shape, as described in (c). The subject would then be placed either inside the fluid filled cavity or in the vest, or sufficiently coupled, acoustically, to the array.

The transducers, the actual preferred amplitudes required for biomedical applications, and a discussion of guidelines for determining the minimum number N of transducers required to realize these amplitudes will next be discussed. It is to be understood, however, the invention is not limited by the following.

It is well known that current lithotripter devices yield a localized pressure of around $1.0 \times 10^8$ Pa (corresponding to a localized Intensity level of $3.38 \times 10^5$ W/cm$^2$, referenced to water as characterizing the medium) in the focal area, for destruction of calculi. Additionally, current research has established a threshold of from $1.438 \times 10^5$ Pa to $2.03 \times 10^5$ Pa (corresponding to a localized Intensity threshold of from 0.7 W/cm$^2$ to 1.4 W/cm$^2$, referenced to water as characterizing the medium), below which free radicals will not be produced in organic fluids. See, e.g., article entitled "Free Radical Production in Aqueous Solutions Exposed to Simulated Ultrasonic Diagnostic Conditions", written by Alasdair J. Carmichael, Magdi M. Mossoba, Peter Riesz, and Christopher L. Christman, published in *IEEE Transactions on Ultrasonics, Ferroelectrics, And Frequency Control*, Vol. UFFC-33, No. 2, Mar. 1986. If it is desired to obtain the large sound amplitude required for calculi destruction, while maintaining a safe level of sound amplitude input by each source such that free radicals will not be produced in the subject, it can be seen then that upon taking the lower level of sound amplitude for the threshold, that since $$\frac{1.0 \times 10^8 \ Pa}{1.438 \times 10^5 \ Pa} = 695.41, \quad \text{Equation (6)}$$

on the order of 695 transducers would be preferred to comprise the array. Thus, if on the order of 695 transducers are used, each emanating a maximum sound pressure equivalent to about $1.438 \times 10^5$ Pa (corresponding to an Intensity level of 0.7W/cm$^2$) calculi will be destroyed in a focal area, without causing damage to intermediary tissue from any single source. This is of course a rough approximation intended for demonstration only, since it neglects effects such as spreading or damping losses in the medium.

Additionally, with reference to FIGS. (2) and (3), and with N=695, for example, 695 linearly independent sound fields ($Y_j$) may be specified at 695 spatial locations (field points) within, or on the medium, and the necessary inputs to each of the transducers may be determined as explained above. It may be desired, for example, that a very large Delta Function spike with an equivalent amplitude (A) of $1.0 \times 10^8$ Pa (corresponding to a localized Intensity level of $3.38 \times 10^5$ W/cm$^2$) occur at a single point at a relative time delay, $\tau$, while simultaneously requiring that another 694 spatial locations immediately surrounding this single point be maintained at zero sound amplitude. In this case:

$$Y_j(t) = \begin{cases} A \times \delta(t - \tau), & \text{if } j = 1; \\ 0, & \text{otherwise.} \end{cases} \quad \text{Equation (7)}$$

This would permit precise, large amplitude sound field specification at a point, while protecting the volume around this point from large amplitude superposition, which may result in damage to the extraneous tissue.

To realize this sort of time dependent resolution and reproduction, the transducers are preferably as broad band as possible in their frequency response, and may be spatially configured so as to realize any of the previous physical descriptions, and to fulfill all of the required causal and linear impulse response features. In particular, if, for example, each of the transducers has a surface area of 1 cm$^2$, therefore supplying a maximum Intensity level of 0.7 W/cm$^2$ (corresponding to a sound pressure of $1.438 \times 10^5$ Pa) per transducer, then the total array of 695 transducers will cover an area equal to 0.0695 M$^2$, or rather 26.36 cm $\times$ 26.36 cm, for example, and deliver the total, localized sound pressure level of $1.0 \times 10^8$ Pa (corresponding to a localized Intensity level of $3.38 \times 10^5 W/cm^2$) required for calculi destruction. In general, the smaller the individual transducers, and correspondingly, the more numerous, the better is the spatial resolution of the specified sound fields. However, there will obviously be a design trade-off between frequency response and transducer size, and practical constraints on the number of linearly independent inputs which may be determined, and simultaneously applied.

In the case of acoustic levitation, or other non-biomedical application, the procedure for field specification is the same, however the impulse response or Green's Function can be calculated and/or measured in a straight forward manner, readily apparent to one of ordinary skill in the art. In particular, it may be desired to control the relative positions of two different fluid droplets in a microgravity environment, such that they may be brought together and combined at a precise mixture rate non-invasively, using acoustic levitation.

A most simple embodiment of this apparatus would be an air filled rectangular enclosure, or cube, of dimensions 20 cm × 20 cm × 20 cm, for example, upon whose 6 interior surfaces are reciprocal transducers, each transducer having dimensions of 1 square centimeter. Some simple arithmetic demonstrates that there may be 2,400 transducers on the inner surface of this cube. From previous discussions, this will permit the specification of an equal number of desired sound fields at an equal number of locations either within, or on the inner surface of the cubical enclosure. To control the vibrational behavior of each of the fluid droplets, the impulse response, or Green's Function, must be determined, and the desired sound fields must be specified. After which, it is a straightforward manner to determine the necessary inputs to the array.

First, the Green's Function for a rectangular enclosure, or the special case of a cubical enclosure, is well known and can be readily found in the literature. Second, it would be most efficient and simple to force the fluid droplets into particular and precise vibrational modes by using the well known technique of the superposition of spherical harmonics, subject to the satisfaction of Equation (1). In this manner, the relative locations of the fluid droplets can be controlled by specifying the relative spatial locations of the desired sound fields which imply or define the presence, location or "flow", and vibrational behavior of the fluid droplets. Additionally, the two fluid droplets may be brought to coexist at the same point within the cube, at a rate of mixture which is controllable through the superposition of the various spherical harmonics. By specifying these sound fields, the necessary inputs to the array can be determined in a manner identical to the previous, biomedical example.

The amplitudes required for the vibrational control of two fluid droplets in free space would, of course, be only a fraction of those required for the previously discussed biomedical example of calculi destruction. Also, adaptation or correction to the Green's Function may be implemented using a similar feedback monitoring loop, however, in the event that appreciable pressures and temperatures result from any chemical reactions caused from the mixture of the various chemicals, which could significantly alter the sound field. In addition, the air, or other gas or fluid filling the enclosure should be kept at a relative, sufficient static pressure so as to:

1. maintain static cohesion of any droplets under manipulation (otherwise evaporation and dissipation of the droplets may occur); and
2. maintain a sufficient propagation medium for acoustic waves.

The foregoing is a description of the preferred embodiments of the present invention. However, the invention is not so limited. Various alternatives will become readily apparent to one of ordinary skill in the art. The invention is only limited by the claims appended hereto.

I claim:

1. A sound wave generating apparatus for destroying or vaporizing undesired objects in a body comprising:
   sound wave generating means for generating sound waves, said sound wave generating means comprising a plurality of transducers; and
   drive means for independently driving each of said plurality of transducers according to a plurality of predetermined inputs to simultaneously effect N desired field point responses at N specified field points, where $N > 1$.

2. The apparatus of claim 1 wherein said plurality of transducers are operatively positioned such that the superposition of all of the generated sound waves at said N specified field points within a sound wave transmission medium produces said N desired sound field responses within, or on the surface of said medium.

3. The apparatus of claim 1 wherein said sound waves are generated with characteristics sufficient to cause the obliteration of lumenal calculi.

4. The apparatus of claim 1 wherein said sound waves are generated with characteristics sufficient to cause the obliteration of atherosclerotic plaque.

5. The apparatus of claim 1 wherein said sound waves are generated with characteristics sufficient to cause the obliteration of vascular thrombi and/or emboli.

6. The apparatus of claim 1 wherein said sound waves are generated with characteristics sufficient to cause the obliteration of small, soft tissue tumors.

7. The apparatus of claim 1 wherein said sound waves are generated with characteristics sufficient to cause the obliteration of hard tissue tumors.

8. The apparatus of claim 1 wherein said sound waves are generated with characteristics sufficient to cause the obliteration of cancerous tissue.

9. The apparatus of claim 1 wherein said sound waves are generated with characteristics sufficient to effect localized cauterization.

10. The apparatus of claim 1 whereas said sound waves are generated with characteristics sufficient to effect generalized, non-invasive percutaneous energy transfer into said body for diagnosis.

11. The apparatus of claim 1 wherein said sound waves are generated with characteristics sufficient to effect generalized, non-invasive percutaneous energy transfer into said body for therapy.

12. A sound wave generating apparatus for destroying or vaporizing undesired objects in a body comprising:
    sound wave generating means for generating sound waves, said sound wave generating means comprising a plurality of transducers, and
    drive means for independently driving each of said plurality of transducers according to a plurality of predetermined inputs; and p1 further comprising means for determining a predicted impulse response characteristic of a sound wave transmission medium, means for specifying a plurality of desired field point responses for a plurality of desired field points and means for determining said plurality of inputs based on said impulse response and said desired field point responses.

13. The apparatus of claim 12 wherein said plurality of transducers comprises an array of N transducers, said desired field points comprise N field points and the means for determining the impulse response comprises means for determining the impulse response of said transmission medium from each of said N transducers to each of said N field points.

14. The apparatus of claim 13 wherein said means for determining the plurality of inputs comprises means for determining the solution to the following equation:

$$\rho(x,y,z)\frac{dv(x,y,z,t)}{dt} = \nabla \cdot I(x,y,z,t).$$

15. The apparatus of claim 14 wherein said drive means provides said plurality of independent inputs based on the solution to the equation set forth in claim 4 and said desired field point responses.

16. The apparatus of claim 15 wherein said plurality of transducers, upon receipt of said plurality of N independent inputs, transmit a plurality of N sound waves such that the superposition of said N sound waves causes the N desired field point responses within or on the surface of said transmission medium.

17. The apparatus of claim 13 wherein said body is a human or animal body.

18. The apparatus of claim 12 wherein said means for determining a predicted impulse response comprises imaging and measurement means for imaging and measuring the spatial distribution and material parameters characteristic of said sound wave transmission medium.

19. The apparatus of claim 18 further comprising processor means for processing data generated by said imaging and measurement means.

20. The apparatus of claim 18 wherein said imaging and measurement means comprises material parameter determining means.

21. The apparatus of claim 18 wherein said imaging and measurement means compromises at least CAT scanning means.

22. The apparatus of claim 18 wherein said imaging and measurement means comprises at least MRI scanning means.

23. The apparatus of claim 12 further comprising means for measuring the actual impulse response at said plurality of transducers, means for comparing said actual impulse response with said predicted impulse response and optimization and monitoring means for minimizing any errors between said actual and predicted impulse responses.

24. The apparatus of claim 23 wherein said optimization and monitoring means comprises adaptive control means and neural network means for optimizing and monitoring the actual impulse response.

25. A method of generating sound waves for destroying or vaporizing undesired objects in a body comprising the steps of:
   determining a predicted impulse response characteristic of a sound wave transmission medium;
   specifying a plurality of desired field point responses;
   determining a plurality of inputs to a plurality of transducers necessary to achieve said desired field point responses for a plurality of desired field points based on said predicted impulse response; and
   independently generating a plurality of sound waves according to said plurality of inputs.

26. The method of claim 25 wherein said step of determining said predicted impulse response comprises determining the impulse response of said transmission medium from each of a plurality of transducers to each of said desired field points.

27. The method of claim 25 further comprising the step of transmitting said plurality of sound waves such that the superposition of said sound waves causes the desired field point responses within or on the surface of said transmission medium.

28. The method of claim 27 wherein the of determining a predicted impulse response comprises the steps of imaging and measuring the spatial distribution and material parameters characteristic of said sound wave transmission medium.

29. The method of claim 28 wherein said steps of imaging and measuring comprises one or more of the following steps:
   performing a CAT scan;
   performing an MRI scan; or
   measuring the material parameters of said medium.

30. The method of claim 27 further comprising the steps of measuring the actual impulse response; comparing said actual impulse response with said predicted impulse response; and optimizing and monitoring the result of the step of comparing to minimize any errors between said actual and predicted impulse responses.

31. The method of claim 27 wherein said sound waves are applied to lumenal calculi to obliterate said calculi.

32. The method of claim 27 wherein said sound waves are applied to gallstones to obliterate said gallstones.

33. The method of claim 27 wherein said sound waves are applied to kidney stones to obliterate said kidney stones.

34. The method of claim 27 wherein said sound waves are applied to atherosclerotic plaque to obliterate said plaque.

35. The method of claim 27 wherein said sound waves are applied to vascular thrombi to obliterate said vascular thrombi.

36. The method of claim 27 wherein said sound waves are applied to deep vein thrombosis to obliterate said deep vein thrombosis.

37. The method of claim 27 wherein said sound waves are applied to pulmonary emboli to obliterate said pulmonary emboli.

38. The method of claim 27 wherein said sound waves are applied to small, soft tissue tumors to obliterate said small, soft tissue tumors.

39. The method of claim 27 wherein said sound waves are applied to lumenal tumors to obliterate said lumenal tumors.

40. The method of claim 27 wherein said sound waves are applied to colonic polyps to obliterate said colonic polyps.

41. The method of claim 27 wherein said sound waves are applied to small endometrial fibroids to obliterate said small endometrial fibroids.

42. The method of claim 27 wherein said sound waves are applied to hard tissue tumors to obliterate said hard tissue tumors.

43. The method of claim 27 wherein said sound waves are applied to bone spurs to obliterate said bone spurs.

44. The method of claim 27 wherein said sound waves are applied to osteophytes to obliterate said osteophytes.

45. The method of claim 27 wherein said sound waves are applied to cancerous tissue to obliterate said cancerous tissue.

46. The method of claim 27 wherein said sound waves are applied to affect local cauterization.

47. The method of claim 27 wherein said sound waves are applied to affect non-invasive percutaneous energy transfer into said body, for diagnosis.

48. The method of claim 27 wherein said step of determining the predicted impulse response is used to obtain a non-invasive characterization of tissues in said body.

49. The method of claim 27 wherein said sound waves are applied to emboli to obliterate said emboli.

50. The method of claim 27 wherein said sound waves are applied to effect non-invasive percutaneous energy transfer into said body for therapy.

* * * * *